United States Patent [19]

Tokuda et al.

[11] Patent Number: 4,765,974

[45] Date of Patent: Aug. 23, 1988

[54] PREPARATION FOR PERCUTANEOUS ADMINISTRATION

[75] Inventors: Shoichi Tokuda; Yuusuke Ito; Saburo Otsuka; Takashi Kinoshita, all of Osaka, Japan

[73] Assignee: Nitto Electric Industrial Co., Ltd., Osaka, Japan

[21] Appl. No.: 48,977

[22] Filed: May 13, 1987

Related U.S. Application Data

[63] Continuation of Ser. No. 813,213, Dec. 24, 1985, abandoned.

[51] Int. Cl.$^4$ .................... A61K 9/70; A61K 31/415; A61L 15/03; A61F 13/02
[52] U.S. Cl. ......................... 424/443; 424/81; 514/386
[58] Field of Search ............ 424/28, 81; 604/896; 514/386

[56] References Cited

U.S. PATENT DOCUMENTS

| | | | |
|---|---|---|---|
| 3,896,789 | 7/1975 | Trancik | 424/28 |
| 4,390,520 | 6/1983 | Nagai et al. | 424/28 |
| 4,409,206 | 10/1983 | Stricker | 424/28 |
| 4,420,470 | 12/1983 | Otsuka et al. | 424/28 |
| 4,552,751 | 11/1985 | Inaka et al. | 424/28 |

FOREIGN PATENT DOCUMENTS

| | | | |
|---|---|---|---|
| 0100715 | 8/1981 | Japan | 424/28 |
| 0183714 | 11/1982 | Japan | 424/28 |
| 0076019 | 4/1984 | Japan | 424/28 |
| 0164714 | 9/1984 | Japan | 424/28 |
| 0028917 | 2/1985 | Japan | 424/28 |
| 1577259 | 10/1980 | United Kingdom | 424/28 |

OTHER PUBLICATIONS

Derwent C82-891398 82.09.17 Nitto.
Derwent 85-285480 85.02.10 Nitto.
Derwent 85-131654 85.04.19 Nitto.

*Primary Examiner*—Glennon H. Hollrah
*Assistant Examiner*—D. Dinner
*Attorney, Agent, or Firm*—Sughrue, Mion, Zinn, Macpeak & Seas

[57] ABSTRACT

A clonidine preparation for percutaneous administration comprising a support having provided thereon an active ingredient-containing layer is disclosed. The active ingredient-containing layer contains an acrylic polymer having a glass transition temperature of from $-70°$ C. to $-10°$ C. and pressure-sensitive adhesion at room temperature as a base, at least one of clonidine and clonidine hydrochloride as an active ingredient, and a decomposition inhibitor. The active ingredient can be stably maintained within the preparation without being decomposed, and, therefore, can be effectively released over a prolonged period of time.

11 Claims, No Drawings

PREPARATION FOR PERCUTANEOUS ADMINISTRATION

This is a continuation of application Ser. No. 06/813,213, filed Dec. 24, 1985, now abandoned.

FIELD OF THE INVENTION

This invention relates to a clonidine preparation for percutaneously administering clonidine or clonidine hyrochloride. More particularly, this invention relates to a clonidine preparation for percutaneous administration, in which decomposition of clonidine is suppressed to ensure satisfactory stability over time, and, upon application onto the skin, that the clonidine and/or clonidine hydrochloride is delivered to veins through the skin to thereby stably maintain a clonidine level in blood over a prolonged period of time.

BACKGROUND OF THE INVENTION

In an attempt to prolong duration of pharmacological effects and to reduce side effects of drugs, percutaneous administration of drugs has recently been increasingly used in place of oral administration or injection. Further, selection of drugs to be administered percutaneously, which had been confined to topical ones, such as antiinflammatory analgesics, has been widened to include an increasing number of systemic drugs. However, it has been extremely difficult to prevent reduction of the content of an active ingredient in preparations with the passage of time, praticularly in that it has been difficult to stably maintain the active ingredient for a long period to time.

Preparations for percutaneous administration containing clonidine or its hydrochloride, which is a percutaneously absorbable systemic drug, are disclosed in U.S. Pat. No. 4,201,211 (corresponding to Japanese Patent Publication No. 20129/79) and Japanese Patent Application (OPI) No. 150614/82 (the term "OPI" as used herein refers to a "published unexamined application"). These preparations achieve the prescribed objects to some extent in terms of controlled release or pharmacological effect, but are still unsatisfactory in terms of stability of the active ingredient for a prolonged period of time.

SUMMARY OF THE INVENTION

An object of this invention is to provide clonidine preparations, in which clonidine and/or clonidine hydrochloride is stably present without being decomposed and can effectively be delivered to the body through the skin.

As a result of extensive and intensive studies to eliminate the above-described problems, it has now been found that stability of clonidine and/or clonidine hydrochloride against decomposition can be remarkably improved by incorporating the active ingredient into an acrylic polymer together with a decomposition inhibitor, whereby reduction in the content of the active ingredient due to instability can be prevented and the pharmacological effect can be maintained. The present invention has been completed based on this finding.

That is, the present invention relates to a clonidine preparation for percutaneous administration comprising a support having provided thereon a layer containing an acrylic polymer having a glass transition temperature of from $-70°$ C. to $-10°$ C. and having pressure-sensitive adhesion at room temperature as a base, at least one of clonidine and clonidine hydrochloride as an active ingredient, and a decomposition inhibitor.

BRIEF DESCRIPTION OF THE ACCOMPANYING DRAWING

FIGURE illustrates a relationship between a clonidine level in blood plasma and time passage when the preparations for percutaneous administration obtained in Examples 1 to 5 were applied to the skin of the human breast.

DETAILED DESCRIPTION OF THE INVENTION

A support which constitutes the preparation for percutaneous administration according to the present invention is not particularly restricted as long as it is suitable for carrying the polymer base layer. Examples of such a support include plastic films or sheets of polyolefin, polyurethane, polyvinyl alcohol, polyvinylidene chloride, polyamide, an ethylene-vinyl acetate copolymer, etc., rubber films or sheets, synthetic resin foamed films or sheets, metal foils, papers, non-woven cloth, woven cloth, and laminates of these materials. It is preferable to use a support having sufficient softness agreeable to the shape or movement of the skin to which the preparation is applied. The thickness of the support is not particularly limited, but is preferably 6 to 300 $\mu$m, and more preferably from 10 to 100 $\mu$m.

Any acrylic polymer having a glass transition temperature of from $-70°$ C. to $-10°$ C. and pressure-sensitive adhesion at room temperature may be employed as a base. Acrylic polymers mainly comprising an acrylic and/or methacrylic (also referred to herein by the terminology "(meth)acrylic") acid alkyl ester having 4 or more carbon atoms in its alkyl moiety are preferred in order to increase availability of the active ingredient and to ensure effective release of the active ingredient. Specific examples of the (meth)acrylic acid alkyl ester having 4 or more carbon atoms in its alkyl moiety are butyl (meth)acrylate, pentyl (meth)acrylate, hexyl (meth)acrylate, heptyl (meth)acrylate, octyl (meth)acrylate, nonyl (meth)acrylate, decyl (meth)acrylate, dodecyl (meth)acrylate, stearyl (meth)acrylate, etc. The alkyl moiety of these esters may be either straight-chain or branched chain alkyl groups. In the production of the acrylic polymer of the present invention, two or more of the above-described ester monomers may be used. The preferred kinds and proportions of main ester monomers to be used can be arbitrarily selected according to the purpose from the above-recited esters and from the range of at least 50% by weight, and more preferably from 50 to 99% by weight, based on the total monomers used.

In addition to the above-mentioned acrylic polymers, copolymers comprising an alkyl (meth)acrylate having 4 or more carbon atoms in its alkyl moiety and a comonomer copolymerizable with alkyl ester monomer are preferably used in view of the desired balance in performance properties, such as adhesion to the skin, cohesion of the acrylic polymer, and the like. Specific examples of such a comonomer include functional monomers, such as carboxyl-containing monomers, e.g., (meth)acrylic acid, maleic acid, maleic anhydride, crotonic acid, etc., hydroxyl-containing monomers, e.g., hydroxyethyl (meth)acrylate, hydroxypropyl (meth)acrylate, etc., amido- or amino-containing monomers, e.g., (meth)acrylamide, dimethylaminoethyl (meth)acrylate, diethylaminoethyl (meth)acrylate, etc., and nitrile-containing monomers, e.g., acrylonitrile; vinyl acetate, vinyl propionate, vinylpyrrolidone, vinylpyridine, vinylimidazole, methoxyethyl (meth)acrylate, ethoxyethyl (meth)acrylate, butoxyethyl (meth)acrylate, and the like. One or more of these comonomers can arbitrarily be selected according to the purpose. A preferred proportion of these comonomers is not more than 50% by weight, and more preferably from 1 to 50% by weight, based on the total monomers used.

Clonidine and clonidine hydrochloride used as the active ingredient in the present invention (alone or in combination) are drugs exhibiting an activity to reduce tonus of the central sympathetic nerveous system and are used for the prevention or treatment of hypertension, hemicrania, and the like. The term "clonidine" as herein used is a common (trivial) name for the compound 2-(2,6-dichloroanilino)-2-imidazoline.

The amount of the active ingredient for percutaneously administering an effective dose is generally from 1 to 25% by weight, and preferably from 2 to 10% by weight, based on the weight of the acrylic polymer.

The decomposition inhibitor used in the present invention is a component which serves to inhibit decomposition of clonidine or clonidine hydrochloride, thereby maintaining the active ingredient in a stable state within the preparation for a long period of time. Examples of such a decomposition inhibitor include organic acids, e.g., citric acid, succinic acid, tartaric acid, maleic acid, fumaric acid, salicyclic acid, acetic acid, etc., and salts thereof. Examples of salts of these organic acids include a salt with sodium, potassium, magnesium, barium, aluminum, etc. of these, citric acid, succinic acid and a sodium or potassium salt thereof are particularly preferred because of their conspicuous decomposition-inhibitory effect. These organic acids or salts thereof are used in an amount of from 0.1 to 5% by weight, and preferably from 1 to 4% by weight, based on the weight of the acrylic polymer. Amounts less than 0.1% by weight are insufficient for producing a desired decomposition-inhibitory effect, and use of too large amounts exceeding 5% by weight does not bring about any further improving effect and also is unfavorable from the viewpoint of skin irritation. Moreover, too large of an amount of the organic acid deteriorates cohesion of the acrylic polymer, which may cause the polymer paste to remain on the skin after removal of the preparation from the skin.

The decomposition inhibitor which can be used in the present invention further includes polyphosphoric acids and salts thereof. These compounds have commonly been utilized as additives for foodstuffs taking advantage of their sequestering activity (metal ion deactivating activity), dispersing activity, activity to prevent crystallization, protein- and pectin-solublizing activity, and the like. When applied to the skin, they have been used in the form of lotions, but are not so suitable for application to the skin due to their high irritant property. However, it has been found that such an irritant property on the skin can significantly be alleviated when the polyphosphoric acids or salts thereof are incorporated in the acrylic polymer according to the present invention. It has also been confirmed that these polyphosphoric acids and salts thereof not only exert a remarkable effect to inhibit decomposition of clonidine or clonidine hydrochloride but also improve percutaneous absorbability of the active ingredient. The polyphosphoric acids which can be used in the present invention are the so-called condensed phosphoric acids and specifically include dipolyphosphoric acid, tripolyphosphoric acid, tetrapolyphosphoric acid, pentapolyphosphoric acid, hexapolyphosphoric acid, ultrapolyphosphoric acid, etc. The salts of these polyphosphoric acids include a salt with sodium, potassium, magnesium, barium, aluminum, etc. In particular, the above-described polyphosphoric acid or a salt thereof preferably has a pH value between the acidic side and a neutral pH (i.e., of from about 2 to about 7) in a 1% by weight aqueous solution. The pH may be adjusted to the above-recited range by addition of a free polyphosphoric acid. These polyphosphoric acids and their salts may be used individually or in combinations of two or more thereof. The amount to be added is generally within the range of from 0.05 to 5% by weight, and preferably from 0.1 to 3% by weight, based on the weight of the acrylic polymer. Amounts out of the aforesaid range are unfavorable, failing to obtain a desired effect on decomposition inhibition or possibly causing irritation on the skin.

The effect to inhibit decomposition of the active ingredient can further be enhanced by combined use of the above-described citric acid, succinic acid and/or a salt thereof, and the polyphosphoric acid and/or a salt thereof. Such a combination being used, they are used in a total amount of from 0.1 to 5% by weight, and preferably from 0.2 to 5% by weight, based on the acrylic polymer at a weight ratio (organic acid and/or a salt thereof/polyphosphoric acid and/or a salt thereof) of 1/0.1 to 1/1. If the weight ratio of the decomposition inhibitors is out of the above range, the effects of the combined use tend to be decreased.

Further, it is possible to ensure effective release of clonidine and/or clonidine hydrochloride from the preparation by adding to the active ingredient-containing layer at least one release aid, such as glycols, e.g., propylene glycol, diethylene glycol, triethylene glycol, polyethylene glycol, polypropylene glycol, etc.; N-methyl-2-pyrrolidone, N-methylpyrrolidone-N-oxide, salicyclic acid, urea, dimethyl sulfoxide, dimethylformamide, diethyl sebacate, ethyl alcohol and a wide variety of surface active agents. From the consideration of a balance between adhesion to the skin and cohesion of the acrylic polymer, these components are preferably added in an amount of from 0.5 to 20% by weight based on the weight of the acrylic polymer.

Since the active ingredient-containing layer comprising the above-described components is adhesive to the skin by itself, the preparation composed of a support and this layer can be applied to the skin without any other aid. The thickness of the active ingredient-containing layer is from 5 to 500 μm, and preferably from 10 to 100 μm in view of a balance of performance properties, such as adhesion to the skin, cohesion of the acrylic polymer, and ease of removal of the preparation from the skin. If the layer thickness is outside of the above range, the balance of performance properties is lost; that is, too small a thickness reduces adhesiveness to the skin, and too large a thickness causes a feeling of disagreement and cannot follow the movement of the skin, leading to falling-off of the preparation during use.

As described above, by incorporating at least one decomposition inhibitor selected from the organic acids and salts thereof, e.g., citric acid, succinic acid and/or sodium and potassium salts thereof, and the polyphosphoric acids and salts thereof into the preparations for percutaneous administration, clonidine and/or clonidine hydrochloride contained as an active ingredient can be stably maintained within the preparations while being prevented from decomposition for a prolonged period of time. Thus, the preparations for percutaneous administration in accordance with the present invention favor to deliver clonidine and/or clonidine hydrochloride in amounts sufficient for treating diseases through the skin to which they are applied.

The present invention will now be illustrated in greater detail with reference to the following examples, but it should be understood that these examples are not limiting the present invention. In these examples, all the parts and percents are given by weight unless otherwise indicated.

EXAMPLE 1

Into a flask, 55 parts of 2-ethylhexyl acrylate, 15 parts of 2-ethoxyethyl acrylate and 30 parts of vinyl acetate were charged, in an inert gas atmosphere. To the system was then added 0.2 part of azobisisobutyronitrile as a polymerization initiator to start polymerization. The polymerization reaction was carried out for about 12 hours while maintaining the inner temperature at from 58° to 62° C. by controlling the stirring speed and the external temperature and by dropping ethyl acetate to thereby obtain a solution of an acrylic polymer having a glass transition temperature of −30° C.

Clonidine and succinic acid were added to the resulting acrylic polymer solution, and the mixture was coated on a release liner to a dry thickness of 50 μm. After drying, the coated layer was transferred onto a polyethylene film support having been subjected to surface oxidation treatment to prepare a clonidine preparation for percutaneous administration. The resulting preparation was found to contain 7.5% of clonidine and 2.5% of succinic acid.

Stability of clonidine in the preparation was evaluated as follows. The preparation was preserved at 50° C. for 3 months in a tight seal, cut in pieces (n=10) and extracted with methanol. The extracted active ingredient was determined by high performance liquid chromatography to obtain a percent remaining of the active ingredient according to the following equation.

$$\text{Percent Remaining (\%)} = \frac{\text{Content After Preservation}}{\text{Content Immediately After Preparation}} \times 100$$

The result obtained is shown in Table 1.

Further, 50 cm² of the clonidine preparation as above obtained was applied to a human breast, and changes in clonidine level in blood plasma with time were observed. The results obtained are shown in FIGURE (.—. line).

EXAMPLE 2

Into a flask, 80 parts of 2-ethylhexyl acrylate and 20 parts of N-vinyl-2-pyrrolidone were charged in an inert gas atmosphere, and 0.3 part of azobisisobutyronitrile was added thereto as a polymerization initiator to effect polymerization. The polymerization reaction was continued for 8 hours while maintaining the inner temperature at from 57 to 60° C. in the same manner as in Example 1 to obtain a solution of an acrylic polymer having a glass transition temperature of −41° C.

Clonidine and citric acid were added to the resulting acrylic polymer solution, and the mixture was coated on a release liner to a dry thickness of 60 μm. After drying, the coated layer was transferred to a polyurethane film support to obtain a clonidine preparation for percutaneous administration. The resulting preparation was found to contain 5% of clonidine and 2% of citric acid.

Stability of clonidine in the preparation and changes in clonidine level in blood when applied to the human breast were determined in the same manner as in Example 1, and the results obtained are shown in Table 1 and FIGURE (o—o line), respectively.

EXAMPLE 3

Into a flask, 95 parts of 2-ethylhexyl acrylate and 5 parts of acrylic acid were charged in an inert gas atmosphere, and 0.3 part of azobisisobutyronitrile was added thereto as a polymerization initiator to effect polymerization. The polymerization was carried out for 8 hours while maintaining the inner temperature at from 58° to 62° C. by the same procedure as in Example 1 to obtain a solution of an acrylic polymer having a glass transition temperature of −43° C.

Clonidine hydrochloride, citric acid, and succinic acid were added to the resulting acrylic polymer solution, and the resulting composition was coated to a release liner at a dry thickness of 40 μm. After drying, the coated layer was transferred to an ethylene-vinyl acetate copolymer film (vinyl acetate content: 22 mol%) to obtain a clonidine preparation for percutaneous administration. The resulting preparation was found to contain 10% of clonidine hydrochloride, 1% of citric acid, and 2% of succinic acid.

Stability of clonidine hydrochloride in the preparation and changes in clonidine level in blood plasma when applied to the human breast were determined in the same manner as in Example 1, and the results obtained are shown in Table 1 and FIGURE (▲—▲ line), respectively.

EXAMPLE 4

A clonidine preparation for percutaneous administration was prepared in the same manner as described in Example 1 except for adding clonidine, succinic acid and tetrapolyphosphoric acid to the acrylic polymer solution. The resulting preparation was found to contain 5% of clonidine, 2% of succinic acid and 2% of tetrapolyphosphoric acid.

Stability of clonidine in the preparation and changes in clonidine level in blood plasma when applied to the human breast were determined in the same manner as in Example 1, and the results obtained are shown in Table 1 and FIGURE (Δ—Δ line), respectively.

EXAMPLE 5

A clonidine preparation for percutaneous administration was prepared in the same manner as in Example 1 except for adding clonidine and potassium tripolyphosphate to the acrylic polymer solution. The resulting preparation was found to contain 5% of clonidine and 4% of potassium tripolyphosphate.

Stability of clonidine in the preparation and changes in clonidine level in blood plasma when applied to the human breast were determined in the same manner as in Example 1, and the results obtained are shown in Table 1 and FIGURE (x—x line), respectively.

COMPARATIVE EXAMPLES 1 TO 5

Clonidine preparations for percutaneous administration were prepared in the same manner as in Examples 1 to 5, except that the decomposition inhibitor or inhibitors added in each of Examples 1 to 5 was or were not used in Comparative Examples 1 to 5, respectively.

Stability of clonidine in each of the resulting comparative preparations was evaluated in the same manner as in Example 1, and the results obtained are shown in Table 1 below.

TABLE 1

| Example No. | Decomposition Inhibitor | Percent Clonidine Remaining (%) |
| --- | --- | --- |
| Example 1 | succinic acid | 99.8 |
| Example 2 | citric acid | 99.2 |
| Example 3 | citric acid + succinic acid | 98.4 |
| Example 4 | succinic acid + tetrapolyphosric acid | 99.4 |
| Example 5 | potassium tripolyphosphate | 99.2 |
| Comparative Example 1 | — | 57.0 |
| Comparative Example 2 | — | 55.7 |
| Comparative Example 3 | — | 65.3 |
| Comparative Example 4 | — | 56.9 |
| Comparative Example 5 | — | 55.2 |

While the invention has been described in detail and with reference to specific embodiments thereof, it will be apparent to one skilled in the art that various changes and modifications can be made therein without departing from the spirit and scope thereof.

What is claimed is:

1. A clonidine preparation for percutaneous administration comprising a support having provided thereon a layer containing an acrylic polymer having a glass transition temperature of from −70° C. to −10° C. and pressure-sensitive adhesion at room temperature as a base, at least one of clonidine and clonidine hydrochloride as an active ingredient, and at least one decomposition inhibitor which inhibits the decomposition of clonidine or clonidine hydrochloride, thereby maintaining the clonidine or clonidine hydrochloride in a stable state within the preparation for a long period of time, wherein said acrylic polymer is a copolymer comprising an alkyl (meth)acrylate having 4 or more carbon atoms in the alkyl moiety thereof, and a monomer copolymerizable with said alkyl (meth)acrylate and said decomposition inhibitor is selected from the group consisting of at least one of citric acid and succinic acid, and sodium and potassium salts thereof.

2. A clonidine preparation for percutaneous administration as in claim 1, wherein said copolymer comprises from 50 to 99% by weight alkyl acrylate.

3. A clonidine preparation for percutaneous administration as in claim 1, wherein said at least one of clonidine and clonidine hydrochloride is or are present in an amount of from 1 to 25% by weight based on the weight of the acrylic polymer.

4. A clonidine preparation for percutaneous administration as in claim 1, wherein at least one of said citric acid and succinic acid, and sodium and potassium salts thereof is present in an amount of from 0.1 to 5% by weight based on the weight of the acrylic polymer.

5. A clonidine preparation for percutaneous administration as in claim 4, wherein at least one of said citric acid and succinic acid, and sodium and potassium salts thereof is present in an amount of from 1 to 4% by weight based on the weight of the acrylic polymer.

6. A clonidine preparation for percutaneous administration as in claim 1, wherein said layer has a thickness of from 5 to 500 μm.

7. A clonidine preparation for percutaneous administration as in claim 6, wherein said layer has a thickness of from 10 to 100 μm.

8. A clonidine preparation for percutaneous administration as in claim 1, wherein said support has a thickness of from 6 to 300 μm.

9. A clonidine preparation for percutaneous administration as in claim 1, wherein said support has a thickness of from 10 to 100 μm.

10. A clonidine preparation for percutaneous administration as in claim 1, wherein said at least one decomposition inhibitor is citric acid, succinic acid or a mixture thereof.

11. A clonidine preparation for percutaneous administration as in claim 3, wherein clonidine is present and the at least one decomposition inhibitor is succinic acid.

* * * * *